(12) United States Patent
Tulshian et al.

(10) Patent No.: US 6,653,315 B2
(45) Date of Patent: Nov. 25, 2003

(54) ADENOSINE $A_{2A}$ RECEPTOR ANTAGONISTS

(75) Inventors: Deen Tulshian, Lebanon, NJ (US); Lisa S. Silverman, Edison, NJ (US); Julius J. Matasi, Monmouth Junction, NJ (US); Eugenia Y. Kiselgof, Flemington, NJ (US); John P. Caldwell, Ringwood, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/269,754

(22) Filed: Oct. 11, 2002

(65) Prior Publication Data
US 2003/0171381 A1 Sep. 11, 2003

Related U.S. Application Data
(60) Provisional application No. 60/329,567, filed on Oct. 15, 2001.

(51) Int. Cl.$^7$ ............ C07D 487/14; A61K 31/519; A61P 9/10; A61P 25/24; A61P 25/28
(52) U.S. Cl. ........................ 514/267; 544/251
(58) Field of Search ............ 544/251; 514/267

(56) References Cited

U.S. PATENT DOCUMENTS

| | | |
|---|---|---|
| 5,565,460 A | 10/1996 | Suzuki et al. |
| 6,288,070 B1 | 9/2001 | Okamura et al. ............ 514/267 |

FOREIGN PATENT DOCUMENTS

| | | |
|---|---|---|
| EP | 0 217 748 | 4/1987 |
| EP | 263071 | 4/1988 |
| EP | 1 227 098 | 7/2002 |
| WO | 95/01356 | 1/1995 |
| WO | 97/05138 | 2/1997 |
| WO | 98/52568 | 11/1998 |
| WO | WO 99/51606 | 10/1999 |
| WO | WO 01/23391 | 4/2001 |
| WO | 01/92264 | 12/2001 |

OTHER PUBLICATIONS

Ungerstedt et al, *Brain Research*, 24 (1970), p. 485–493.
Ungerstadt, *Eur. J. Pharmacol.*, 5 (1968), p. 107–110.
*Chemical Abstracts*, 120 (1994) 323446r.
Baraldi et al, *J. Med. Chem.*, 39 (1996) 1164–1171.
Dionisotti et al, *Br. J. Pharmacol.*, 112 (1994) 659–665.
Ongini, *Drug Dev. Res.*, 42 (1997) 63–70.
Negretti et al, *Res. Comm. Molecular Path. and Pharmacol.*, 87 (1995).
Gatta et al, *J. Heterocyclic Chem.*, 31 (1994) 1171–1176.
Okamura et al, *J. Med. Chem.*, 45 (2002) 3703–3708.

*Primary Examiner*—Mukund J. Shah
*Assistant Examiner*—Venkataraman Balasubramanian
(74) *Attorney, Agent, or Firm*—Anita W. Magatti

(57) ABSTRACT

Compounds having the structural formula I

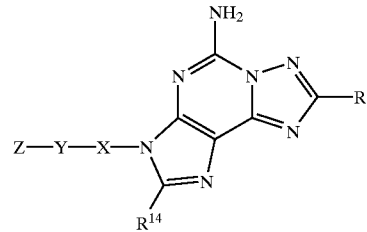

or a pharmaceutically acceptable salt thereof, wherein
R is optionally substituted phenyl or heteroaryl, cycloalkenyl, —C(=CH$_2$)CH$_3$, —C≡C—CH$_3$, —CH=C(CH$_3$)$_2$,

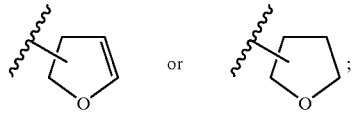

X is alkylene, —C(O)CH$_2$— or —C(O)N(R$^2$)CH$_2$—;
Y is —N(R$^2$)CH$_2$CH$_2$N(R$^3$)—, —OCH$_2$CH$_2$N(R$^2$)—, —O—, —S—, —CH$_2$S—, —(CH$_2$)$_2$—N(R$^2$)—, or optionally substituted divalent heteroaryl, piperidinyl or piperazinyl; and
Z is optionally substituted phenyl, phenylalkyl or heteroaryl, diphenylmethyl or R$^6$—C(O)—;
or when Y is

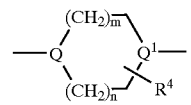

Z is also R$^6$—SO$_2$—, R$^7$—N(R$^8$)—C(O)—, R$^7$—N(R$^8$)—C(S)— or R$^6$OC(O)—;
or when Y is 4-piperidinyl, Z can be phenylamino or pyridylamino; or
Z and Y together are substituted piperidinyl, substituted pyrrolidinyl or substituted phenyl;
R$^{14}$ is H, halogen or optionally substituted alkyl; and
Q, Q$^1$, m, n, R$^2$, R$^3$, R$^4$, R$^6$, R$^7$ and R$^8$ are as defined in the specification are disclosed, their use in the treatment of Parkinson's disease, alone or in combination with other agents for treating Parkinson's disease, and pharmaceutical compositions comprising them.

15 Claims, No Drawings

ADENOSINE $A_{2A}$ RECEPTOR ANTAGONISTS

CROSS REFERENCE TO RELATED APPLICATONS

This application claims the benefit of US Provisional Application No. 60/329,567, filed Oct. 15, 2001.

BACKGROUND

The present invention relates to substituted 5-amino-imidazolo-[4,3-e]-1,2,4-triazolo[1,5-c]pyrimidine adenosine $A_{2a}$ receptor antagonists, the use of said compounds in the treatment of central nervous system diseases, in particular Parkinson's disease, and to pharmaceutical compositions comprising said compounds.

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ are high-affinity, inhibiting the activity of the enzyme adenylate cyclase, and $A_{2a}$ and $A_{2b}$ are low-affinity, stimulating the activity of the same enzyme. Analogs of adenosine able to interact as antagonists with the $A_1$, $A_2$, $A_{2b}$ and $A_3$ receptors have also been identified.

Selective antagonists for the $A_{2a}$ receptor are of pharmacological interest because of their reduced level of side affects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses of organic origin.

Some xanthine-related compounds have been found to be $A^1$ receptor selective antagonists, and xanthine and non-xanthine compounds have been found to have high $A_{2a}$ affinity with varying degrees of $A_{2a}$ vs. $A_1$ selectivity. Triazolo-pyrimidine adenosine $A_{2a}$ receptor antagonists with different substitution at the 7-position have been disclosed previously, for example in WO 95/01356; U.S. Pat. No. 5,565,460; WO 97/05138; WO 98/52568 and US Provisional Application 60/334,342. Pyrazolo-substituted triazolo-pyrimidine adenosine $A_{2a}$ receptor antagonists are disclosed in WO 01/92264.

SUMMARY OF THE INVENTION

The present invention relates to a compound represented by the structural formula I

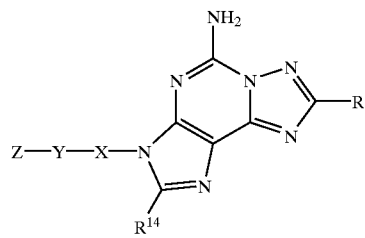

or a pharmaceutically acceptable salt thereof, wherein

R is $R^1$-heteroaryl, $R^{10}$-phenyl, $C_4$-$C_6$ cycloalkenyl, —C(=CH$_2$)CH$_3$, —C≡C—CH$_3$, —C≡C—CH$_2$—OR$^2$, —CH=C(CH$_3$)$_2$,

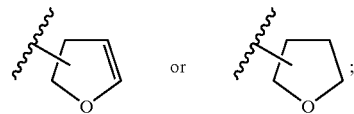

X is $C_1$-$C_6$ alkylene, —C(O)CH$_2$— or —C(O)N(R$^2$)CH$_2$—;

Y is —N(R$^2$)CH$_2$CH$_2$N(R$^3$)—, —OCH$_2$CH$_2$N(R$^2$)—, —O—, —S—, —CH$_2$S—, —(CH$_2$)$_{2-3}$N(R$_2$)—, $R^5$-divalent heteroaryl,

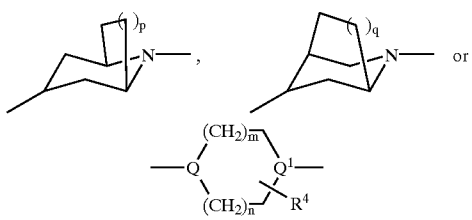

and Z is $R^5$-phenyl, $R^5$-phenyl($C_1$-$C_6$)alkyl, $R^5$-heteroaryl, $R^5$-bicyclic heteroaryl, $R^5$-benzofused heteroaryl, diphenylmethyl or $R^6$—C(O)—;

or when Y is

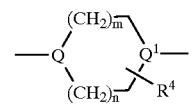

Z is also $R^1$—SO$_2$—, $R^7$—N(R$^8$)—C(O)—, $R^7$—N(R$^8$)—C(S)— or $R^6$OC(O)—;

or when Q is

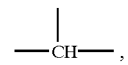

Z is also phenylamino or pyridylamino;

or Z and Y together are

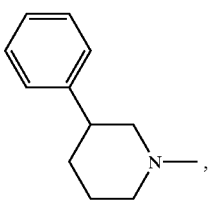 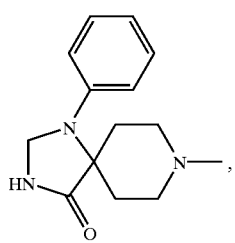

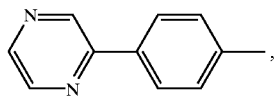 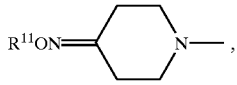

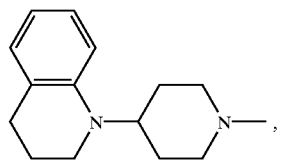

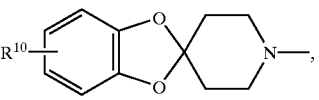

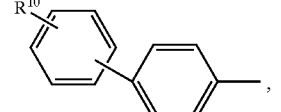

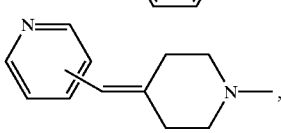

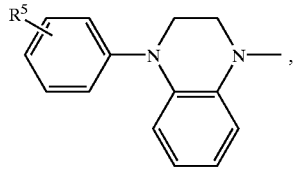

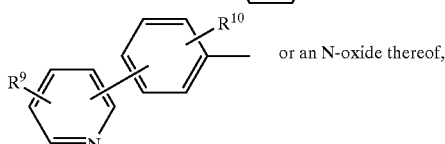 or an N-oxide thereof,

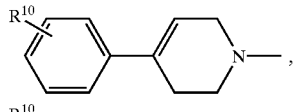

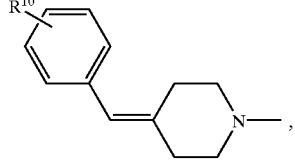

or Y and Z together form a piperidinyl or pyrrolidinyl ring fused to a monocyclic or bicyclic aryl or a monocyclic or bicyclic heteroaryl ring wherein X is attached to the N atom of the piperidinyl or pyrrolidinyl ring;

$R^1$ is 1 to 3 substituents independently selected from hydrogen, $C_1$-$C_6$-alkyl, —$CF_3$, halogen, —$NO_2$, —$NR^{12}R^{13}$, $C_1$-$C_6$ alkoxy, $C_1$-$C_6$ alkylthio, $C_1$-$C_6$ alkylsulfinyl, $C_1$-$C_6$ alkylsulfonyl, —$COOR^7$ or —$C(O)NR^2R^3$;

$R^2$ and $R^3$ are independently selected from the group consisting of hydrogen and $C_1$-$C_6$ alkyl;

m and n are independently 2–3;

p and q are independently 0–2;

Q and $Q^1$ are independently selected from the group consisting of

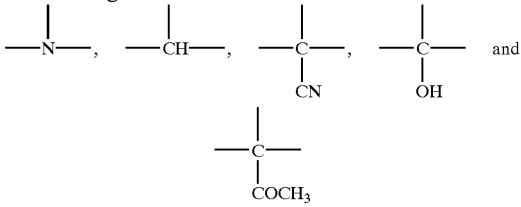

provided that at least one of Q and $Q^1$ is

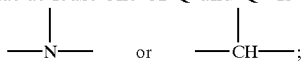

$R^4$ is 1–2 substituents independently selected from the group consisting of hydrogen, $C_1$-$C_6$alkyl, $R^1$-aryl and $R^1$-heteroaryl, or two $R^4$ substituents on the same carbon can form =O;

$R^5$ is 1 to 5 substituents independently selected from the group consisting of hydrogen, halogen, $C_1$-$C_6$ alkyl, hydroxy, $C_1$-$C_6$ alkoxy, —CN, di—(($C_1$-$C_6$)alkyl) amino, —$CF_3$, —$OCF_3$, acetyl, —$NO_2$, hydroxy ($C_1$-$C_6$)alkoxy, ($C_1$-$C_6$)-alkoxy($C_1$-$C_6$)alkoxy, di—(($C_1$-$C_6$)-alkoxy)($C_1$-$C_6$)alkoxy, ($C_1$-$C_6$)-alkoxy ($C_1$-$C_6$)alkoxy—($C_1$-$C_6$)-alkoxy, carboxy($C_1$-$C_6$)-alkoxy, ($C_1$-$C_6$)-alkoxycarbonyl($C_1$-$C_6$)alkoxy, ($C_3$-$C_6$)cycloalkyl($C_1$-$C_6$)alkoxy, di—(($C_1$-$C_6$)alkyl) amino($C_1$-$C_6$)alkoxy, morpholinyl, ($C_1$-$C_6$)alkyl— $SO_2$—, ($C_1$-$C_6$)alkyl—$SO_2$-($C_1$-$C_6$)alkoxy, tetrahydropyranyloxy, ($C_1$-$C_6$)alkylcarbonyl($C_1$-$C_6$)- alkoxy, ($C_1$-$C_6$)-alkoxycarbonyl, ($C_1$-$C_6$) alkylcarbonyloxy($C_1$-$C_6$)-alkoxy, —$SO_2NH_2$, phenoxy,

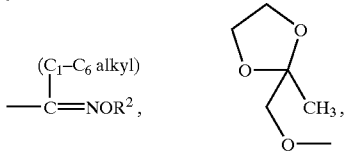

($R^2O)_2$—P(O)—$CH_2$—O— and ($R^2O)_2$—P(O)—; or adjacent $R^5$ substituents together are —O—$CH_2$— O—, —O—$CH_2CH_2$—O—, —O—$CF_2$—O— or —O—$CF_2CF_2$—O— and form a ring with the carbon atoms to which they are attached;

$R^6$ is ($C_1$-$C_6$)alkyl, $R^5$-phenyl, $R^5$-phenyl($C_1$-$C_6$)alkyl, thienyl, pyridyl, ($C_3$-$C_6$)—cycloalkyl, ($C_1$-$C_6$)alkyl— OC(O)—NH—($C_1$-$C_6$)alkyl—, di—(($C_1$-$C_6$)alkyl) aminomethyl, or

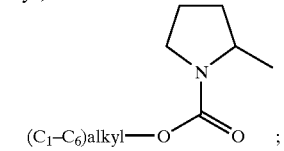

$R^7$ is ($C_1$-$C_6$)alkyl, $R^5$-phenyl or $R^5$-phenyl($C_1$-$C_6$)alkyl;

$R^8$ is hydrogen or $C_1$-$C_6$ alkyl; or $R^7$ and $R^8$ together are —($CH_2)_p$—A—($CH_2)_q$, wherein p and q are independently 2 or 3 and A is a bond, —$CH_2$—, —S—or —O—, and form a ring with the nitrogen to which they are attached;

$R^9$ is 1–2 substituents independently selected from the group consisting of hydrogen, $C_1$-$C_6$ alkyl, hydroxy, $C_1$-$C_6$ alkoxy, halogen, —$CF_3$ and ($C_1$-$C_6$)alkoxy-($C_1$-$C_6$)alkoxy;

$R^{10}$ is 1 to 5 substituents independently selected from the group consisting of hydrogen, halogen, $C_1$-$C_6$ alkyl, hydroxy, $C_1$–$C_6$ alkoxy, —CN, —$NH_2$, $C_1$–$C_6$alkylamino, di—(($C_1$–$C_6$)alkyl)amino, —$CF_3$, —$OCF_3$, —$S(O)_{0-2}$($C_1$–$C_6$)alkyl and —$CH_2$—$SO_2$-phenyl;

$R^{11}$ is H, $C_1$–$C_6$ alkyl, phenyl, benzyl, $C_2$–$C_6$ alkenyl, $C_1$–$C_6$ alkoxy($C_1$–$C_6$)alkyl, di-(($C_1$–$C_6$)alkyl)amino ($C_1$–$C_6$)alkyl, pyrrolidinyl($C_1$–$C_6$)alkyl or piperidino ($C_1$–$C_6$)alkyl;

$R^{12}$ is H or $C_1$–$C_6$ alkyl;

$R^{13}$ is H, ($C_1$–$C_6$)alkyl—C(O)— or ($C_1$–$C_6$)alkyl—$SO_2$—;

$R^{14}$ is H, halogen, $C_1$–$C_6$ alkyl, hydroxy($C_1$–$C_6$)alkyl, $C_1$–$C_6$ alkoxy($C_1$–$C_6$)alkyl, thio($C_1$–$C_6$)alkyl, ($C_1$–$C_6$)alkylthio($C_1$–$C_6$)alkyl or $NR^2R^3$—($C_1$–$C_6$)alkyl; and $R^{15}$ is H, halogen, $C_1$–$C_6$ alkyl or $C_1$–$C_6$ alkoxy.

Another aspect of the invention is a pharmaceutical composition comprising a therapeutically effective amount of a compound of formula I in a pharmaceutically acceptable carrier.

Yet another aspect of the invention is a method of treating central nervous system diseases such as depression, cognitive diseases and neurodegenerative diseases such as Parkinson's disease, senile dementia or psychoses of organic origin, or stroke, comprising administering a compound of formula I to a mammal in need of such treatment. In particular, the invention is drawn to the method of treating Parkinson's disease comprising administering a compound of formula I to a mammal in need of such treatment.

Still another aspect of the invention is a method of treating Parkinson's disease with a combination of a compound of formula I and one or more agents useful in the treatment of Parkinson's disease, for example dopamine; a dopaminergic agonist; an inhibitor of monoamine oxidase, type B (MAO-B); a DOPA decarboxylase inhibitor (DCI); or a catechol-O-methyltransferase (COMT) inhibitor. Also claimed is a pharmaceutical composition comprising a compound of formula I and one or more agents known to be useful in the treatment of Parkinson's in a pharmaceutically acceptable carrier.

DETAILED DESCRIPTION

Referring to compounds of formula I above, preferred compounds of formula I are those wherein R is $R^1$-furanyl, $R^1$-thienyl, $R^1$-pyrrolyl, $R^1$-pyridyl or $R^{10}$-phenyl, more preferably $R^1$-furanyl or $R^{10}$-phenyl. $R^1$ is preferably hydrogen or halogen. $R^{10}$ is preferably hydrogen, halogen, alkyl or —$CF_3$. Another group of preferred compounds is that wherein X is alkylene, preferably ethylene. Y is preferably

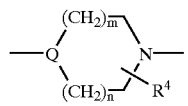

wherein Q is

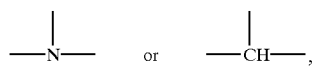

with Q preferably being nitrogen. Preferably, m and n are each 2, and $R^4$ is H. A preferred definition for Z is $R^5$-phenyl or $R^5$-heteroaryl. $R^5$ is preferably H, halogen, alkyl, alkoxy, hydroxyalkoxy or alkoxyalkoxy. $R^6$ is preferably $R^5$-phenyl. $R^{14}$ is preferably hydrogen.

When Y and Z together form a piperidinyl or pyrrolidinyl ring fused to a monocyclic or bicyclic aryl or heteroaryl ring, preferred fused ring structures are

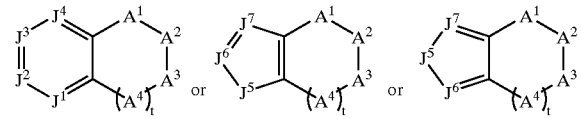

wherein $A^1$ is

and $A^2$ and $A^3$ each are —$C(R^{16})(R^{17})$—, or
$A^1$ and $A^3$ each are —$C(R^{16})(R^{17})$— and $A^2$ is

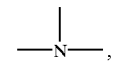

or
$A^1$ and $A^2$ each are —$C(R^{16})(R^{17})$—, and $A^3$ is

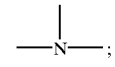

$A^4$ is —$C(R^{16})(R^{17})$—;
$J^1$, $J^2$, $J^3$ and $J^4$ are selected from the group consisting of —N= and —$C(R^{18})$—, provided that 0–2 of $J_1$, $J^2$, $J^3$ or $J^4$ are —N= and the remainder are —$C(R^{18})$—;
$J^5$ is —$N(R^{17})$—, —O—, —S— or —$C(R^{16})(R^{17})$—;
$J^6$ is —N= or —$C(R^{18})$—;
$J^7$ is —N= or —$C(R^{18})$—;
t is 0 or 1;
each $R^{16}$ is independently selected from the group consisting of hydrogen, $C_1$–$C_6$-alkyl, $C_1$–$C_6$-alkoxy, —$CF_3$, halogen, —OH and $NO_2$;
each $R^{17}$ is independently selected from the group consisting of hydrogen and $C_1$–$C_6$ alkyl; and
each $R^{18}$ is independently selected from the group consisting of hydrogen, $C_1$–$C_6$-alkyl, $CF_3$, halogen, $NO_2$, $C_1$–$C_6$-alkoxy, —O—C(O)—($C_1$–$C_6$-alkyl), —$NH_2$, —NH($C_1$–$C_6$-alkyl), —N($C_1$–$C_6$-alkyl)$_2$, —NH—C(O)—($C_1$–$C_6$-alkyl), —NH—$SO_2$—($C_1$–$C_6$-alkyl), —$SO_2$NH($C_1$–$C_6$-alkyl), —$SO_2$N($C_1$–$C_6$-alkyl)$_2$, —$SO_2NH_2$ and —OH.

In the above structures, when $A^1$, $A^2$ or $A^3$ is

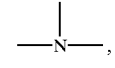

two of the bonds are part of the ring and the third bond joins the ring to the variable X.

In the definition of Q and $Q^1$,

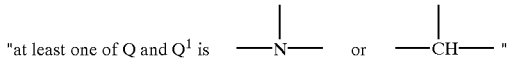

means that one of Q and $Q^1$ can be nitrogen and the other is selected from the remaining groups, both are nitrogen, both are CH, or one is CH and the other is selected from the remaining groups.

As used herein, the term alkyl includes straight or branched chains. Alkylene, referring to a divalent alkyl group, similarly refers to straight or branched chains. Cycloalkylene refers to a divalent cycloalkyl group. Cycloalkenyl refers to a $C_4$–$C_6$ cycloalkyl ring comprising one double bond.

Aryl means phenyl or naphthyl.

Heteroaryl means a single ring heteroaromatic group of 5 to 6 atoms comprised of 2 to 5 carbon atoms and 1 to 3 heteroatoms independently selected from the group consisting of N, O and S, provided that the rings do not include adjacent oxygen and/or sulfur atoms. Examples of single-ring heteroaryl groups are pyridyl, oxazolyl, isoxazolyl, oxadiazolyl, furanyl, pyrrolyl, thienyl, imidazolyl, pyrazolyl, thiazolyl, isothiazolyl, thiadiazolyl, pyrazinyl, pyrimidyl, pyridazinyl and triazolyl. Bicyclic heteroaryl means a bicyclic heteroaromatic group of 5 to 10 atoms comprised of 1 to 9 carbon atoms and 1 to 3 heteroatoms independently selected from the group consisting of N, O and S, provided that the rings do not include adjacent oxygen and/or sulfur atoms. Examples of bicyclic heteroaryl groups are naphthyridyl (e.g., 1, 5 or 1,7), imidazopyridyl, pyrido[2,3]imidazolyl, pyridopyrimidinyl and 7-azaindolyl. Benzofused heteroaryl bicyclic groups comprise a heteroaryl ring as defined above fused at adjacent carbon atoms to a phenyl ring. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 2-pyridyl, 3-pyridyl and 4-pyridyl. N-oxides of the ring nitrogens for all heteroaryl groups are also included. $R^5$-substituted heteroaryl refers to such groups wherein substitutable ring carbon atoms have a substituent as defined above.

Divalent heteroaryl means a heteroaryl ring bonded to two different groups. In the context of this invention, when Y is divalent $R^5$-heteroaryl, one ring member is attached to the variable X, and another ring member is attached to variable Z; the $R^5$ substituents are attached to the remaining ring members. Divalent heteroaryl groups are named by adding "diyl" to the name of the ring, for example, a pyridinediyl ring is shown:

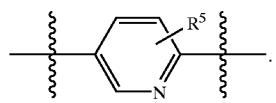

Certain compounds of the invention may exist in different stereoisomeric forms (e.g., enantiomers, diastereoisomers and atropisomers). The invention contemplates all such stereoisomers both in pure form and in mixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of formula I are prepared by methods known in the art. Preferably, the compounds of formula I are prepared by the methods shown in the following reaction schemes.

In the reaction schemes and the examples that follow, the following abbreviations are used: Ts (tosyl); Bn (benzyl); Me (methyl); Et (ethyl); and Ac (acetyl).

In Scheme 1, alkylation of a 5-amino-imidazolo[4,3-e]-[1,2,4]-triazolo-[1,5-c]pyrimidine of formula II is used to prepare compounds of formula I:

Scheme 1:

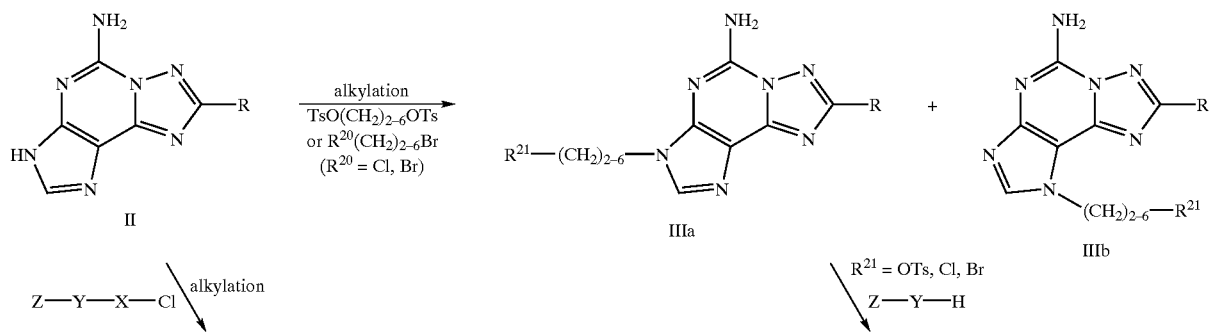

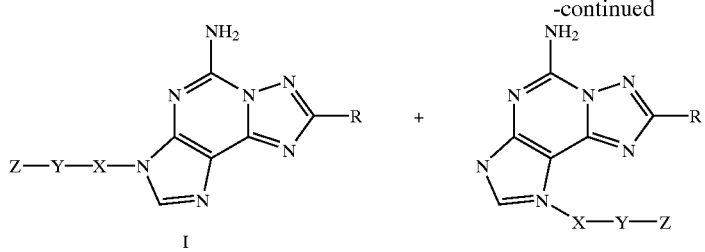
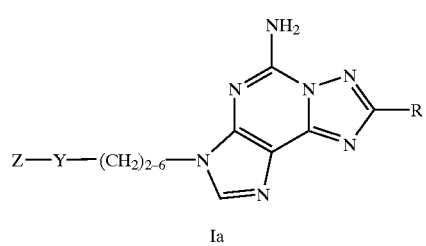

Starting materials of formula II can be reacted with an alkyl diol ditosylate and a base such as NaH in an inert solvent such as dimethylformamide (DMF), or with a chloro-bromo- or dibromo-alkyl compound under similar conditions, to obtain the 7- and 9-alkyl-substituted intermediates of formula IIIa and III b. The compound of formula IIIa is then reacted with an amine of the formula Z—Y—H in an inert solvent such as DMF at an elevated temperature to obtain a compound of formula Ia, i.e., a compound of formula I wherein X is alkylene.

Alternatively, starting materials of formula II can be reacted with a compound of formula Z—Y—X—Cl and a base such as NaH in an inert solvent such as DMF to obtain a mixture of a 7-substituted compound of formula I and the corresponding 9-substituted compound.

Compounds of formula II can be prepared using the general procedure described in Scheme 2.

Scheme 2:

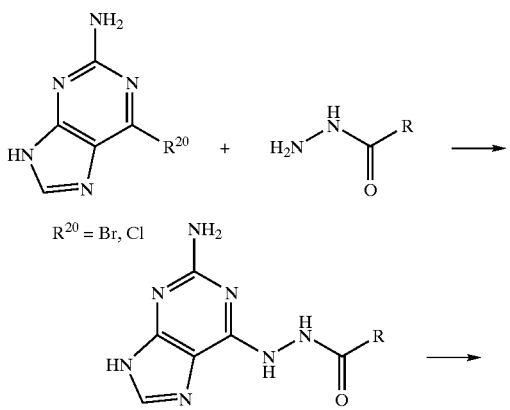

Commercially available 2-amino-6-bromo purine or 2-amino-6-choloro purine can be reacted with the corresponding hydrazide in butanol at elevated temperatures to produce the displacement product, which can be treated with N,O-bis (trimethylsilyl) acetamide to produce II.

To prepare compounds of formula I wherein Y is piperazinyl and Z is $R^6$—C(O)—, $R^6$—SO$_2$—, $R^6$—OC(O)—, $R^7$—N($R^8$)—C(O)— or $R^7$—N($R^8$)—C(S)—, a compound of formula I wherein Z—Y is 4-t-butoxycarbonyl-1-piperazinyl is deprotected, for example by reaction with an acid such as HCl. The resultant free piperazinyl compound, IV, is treated according to procedures well known in the art to obtain the desired compounds. The following Scheme 3 summarizes such procedures:

Scheme 3:

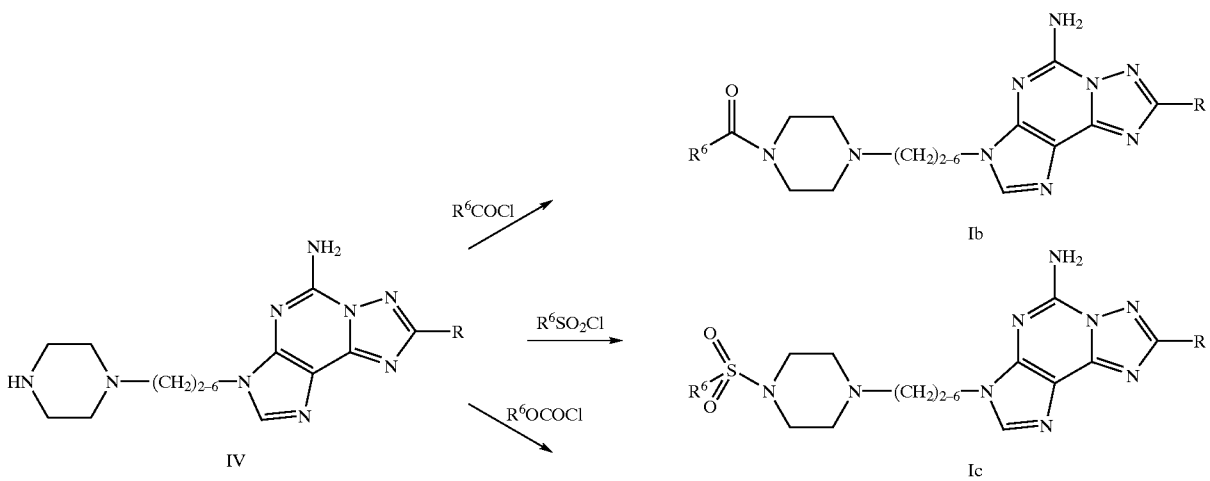

-continued

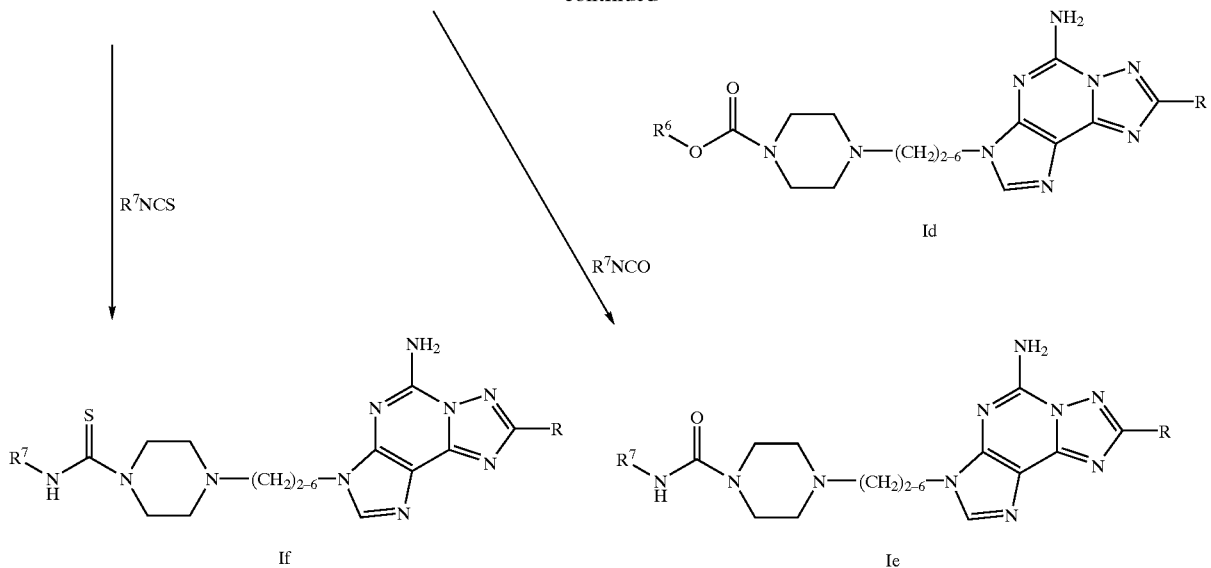

Another method for preparing compounds of formula I is shown in Scheme 4:

Scheme 4:

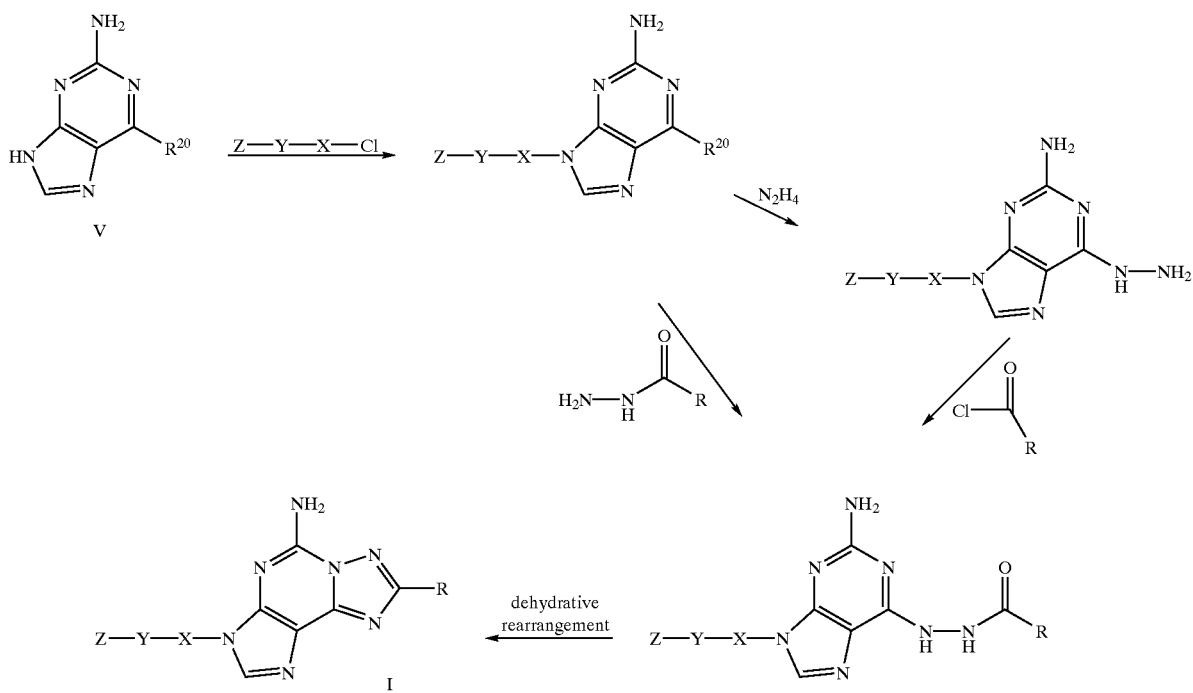

In this procedure, chloroimidazo-pyrimidine V, wherein $R^{20}$ is as defined above, is reacted with a compound of formula Z—Y—X—Cl in a manner similar to the alkylation procedure of Scheme 1, and the resultant intermediate is reacted with a hydrazide of formula $H_2N$—NH—C(O)—R (or with hydrazine hydrate, followed by a compound of formula Cl—C(O)—R). The resultant hydrazide undergoes dehydrative rearrangement, e.g., by treatment with N,O-bis-(trimethylsilyl)acetamide (BSA) or a combination of BSA and hexamethyldisilazane (HMDS) and at elevated temperatures.

Starting materials are known or are prepared by processes known in the art.

Another method for preparing compounds of formula I is illustrated in the following Scheme 5:

Scheme 5:

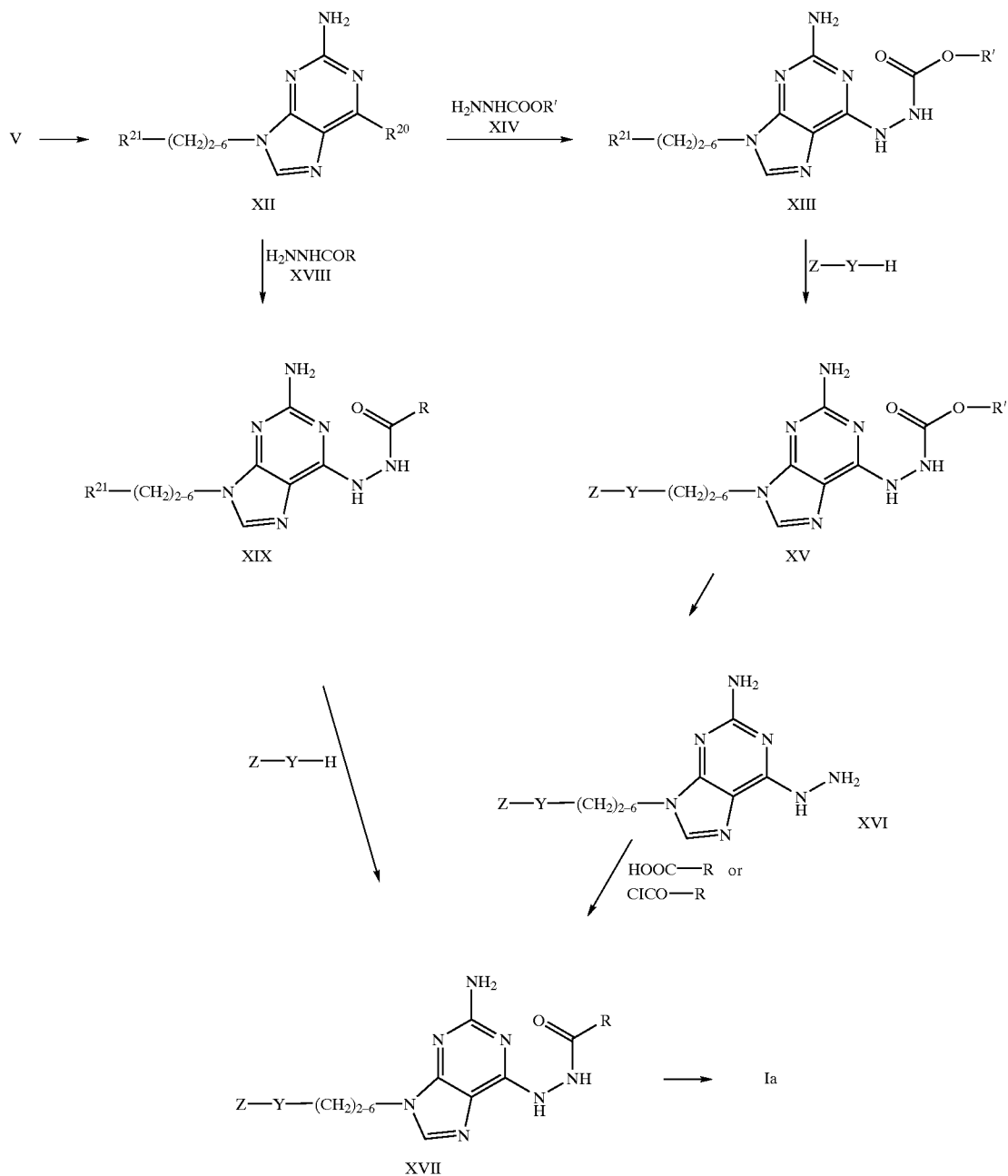

In analogy to Scheme 1, chloride V is converted into alkylated compound XII, and this is further reacted with XIV, where R' is preferably t-butyl or benzyl, to obtain derivative XIII. A solvent such as DMF may be employed at a temperature of 60–120° C. This is then reacted as in Scheme 1 to furnish XV. The R' group is next removed, such as removal of a t-butyl group with HCl or trifluoroacetic acid (TFA), furnishing hydrazine XVI. Acylation of XVI furnishes XVII, which is subjected to dehydrative cyclization as described above to provide desired Ia. Alternatively, XII may be reacted with a hydrazide XVIII to obtain XIX, which can be converted to XVII analogously to preparation of XV.

To prepare compounds of formula IIa, wherein $R^{14}$ is other than hydrogen, the following procedure can be used:

Scheme 6:

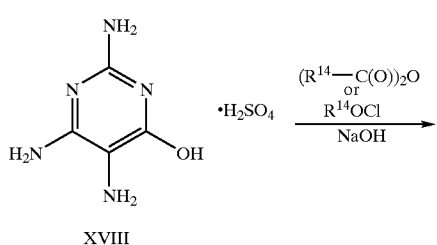

-continued

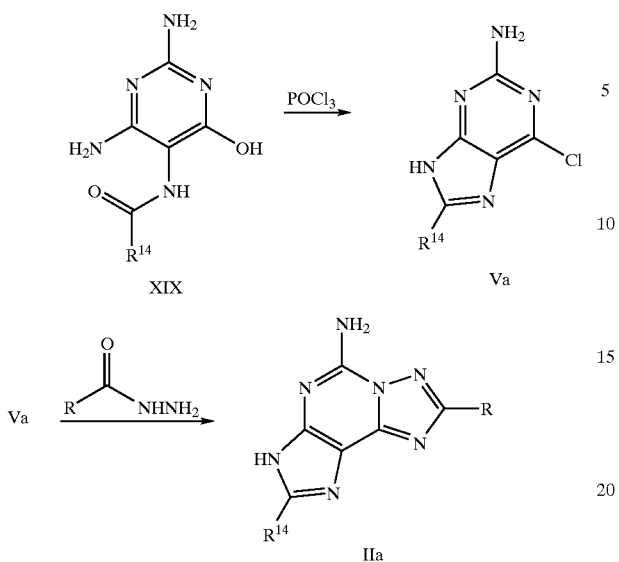

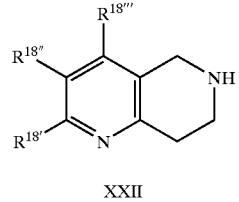

Benzyl piperidinone is cyclized with an aminoacrylaldehyde of formula XX to form the benzyl protected tetrahydronaphthyridine of formula XXI, followed by hydrogenolysis to obtain the compound of formula XXII.

Scheme 8:

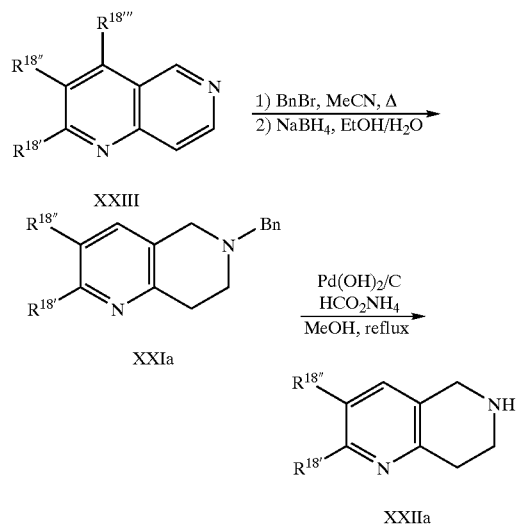

The amide of formula XIX is prepared by reacting the pyrimidine of formula XVIII and the acid chloride or anhydride in the presence of a base such as NaOH, and the compound of formula XIX is then cyclized using a reagent such as POCl₃ to obtain the chloroimidazolo-pyrimidine of formula Va. The compound of formula Va is reacted with the hydrazide as described in Scheme 2 to obtain the intermediate IIa, which can then be used to prepare a compound of formula I as described in Scheme 1. Compound XVIII, the acid chlorides and the hydrazines are known or can be prepared by processes known in the art.

Schemes 7 to 10 show procedures for preparing starting materials for compounds wherein Y and Z together form an aryl- or heteroaryl- fused piperidinyl or pyrrolidinyl group. The resultant Y—Z portions can be reacted with a compound of formula IIIa as described in Scheme 1 to obtain the desired compounds of formula I. The aromatic portions of the fused ring groups are substituted by independently selected $R^{18}$ groups, designated in the schemes as $R^{18'}$, $R^{18''}$ and $R^{18'''}$.

Quaternization of a naphthyridine of formula XXIII followed by reduction gives a benzyl protected tetrahydronaphthyridine of formula XXIa. Hydrogenolysis provides the desired product of formula XXIIa.

Scheme 9:

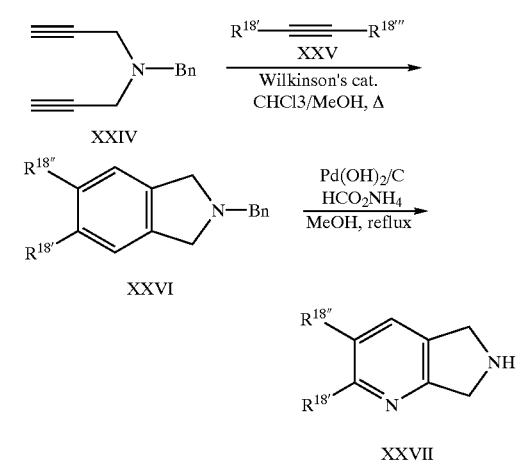

Scheme 7:

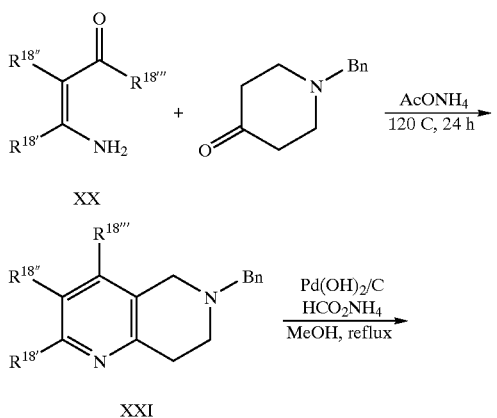

[2+2+2] cyclization of a diyne of formula XXIV with an acetylene of formula XXV provides the benzyl protected isoindoline of formula XXVI. Hydrogenolysis provides the desired compound of formula XXVII.

Scheme 10:

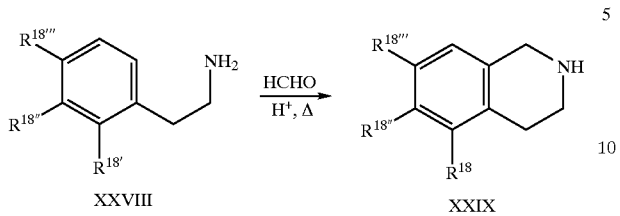

Pictet-Spengler cyclization of a phenethylamine of formula XXVIII gives a substituted tetrahydroisoquinoline of formula XXIX.

Using the above procedures, the following compounds were prepared.

Preparation 1

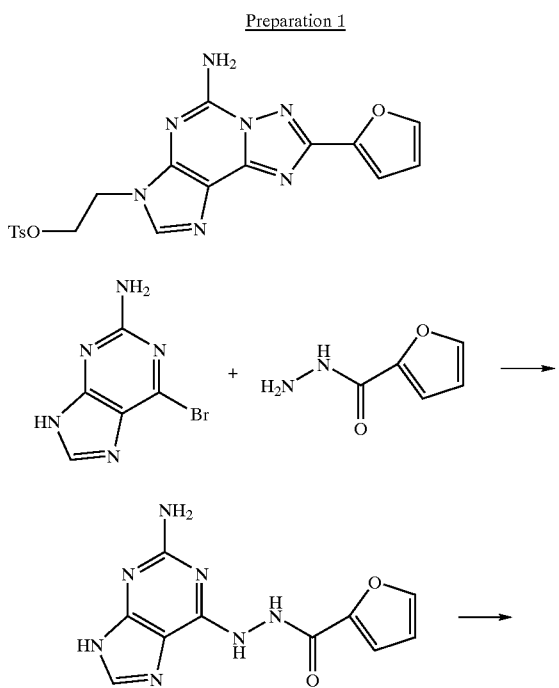

Step 1: Heat a mixture of 2-amino-6-bromo purine (1.0 g, 4.7 mmol) and 2-furoic hydrazide (0.88 g, 7.0 mmol) in butanol (10 ml) at 120° C. overnight. Collect the solid by filtration, wash with $CH_3OH$ and dry the solid in vacuum oven to produce a white solid. MS (ESI): M+1=260.1. PMR (DMSO) δ 6.71 (d, J=1.6 Hz, 1H), 7.32 (s, 1H), 7.41 (bs, 2H), 7.96 (s, 1H), 8.19 (s, 1H), 10.40 (bs, 1H), 10.86 (s, 1H).

Step 2: Heat the product of Step 1(1.3 g, 5 mmol) in N, O-bis (trimethylsilyl) acetamide (6.10 g, 30 mmol) at 100° C. overnight. Cool the reaction mixture and pour it on ice water and stir for 4 h. Collect the solid by filtration and wash with $CH_3OH$, $Et_2O$ and dry to produce a white solid.

MS(ESI): M+1=242. PMR(DMSO) δ 6.71 (dd, J=1.7 & 3.4 Hz, 1H), 7.21 (d, J=2.9 Hz, 1H), 7.67 (s, 1H), 7.92 (s, 1H), 7.99 (s, 1H).

Step 3: Combine the product of Step 2 (5.0 g, 20.7 mmol) and ethylene glycol ditosylate (8.45 g, 22.8 mmol ) in dry DMF (30 ml). Cool the reaction mixture to 0° C. under $N_2$. Add NaH (60% in oil, 0.91 g, 22.8 mmol) in portions, keeping internal temperature at 0° C. Warm the reaction mixture to room temperature and stir overnight. Pour the reaction mixture on ice/water and stir for 4 h. Collect the solid by filtration and chromatograph it on silica gel to produce the title compound.

MS (ESI): M+1=440.10, PMR (DMSO) δ 1.98 (s, 3H), 4.38 (d, J=4.3 Hz, 2H), 4.47 (t, J=4.4 Hz, 2H), 6.72 (dd, J=1.7 & 3.4 Hz, 1H), 6.96 (d, J=8.1 Hz, 2H), 1H), 7.32 (d, J=8.2 Hz, 2H), 7.73 (s, 2H), 7.93 (s, 1H), 7.94 (d, J=0.8

In a similar manner to Preparation 1, but employing the corresponding hydrazide, the following compounds were prepared:

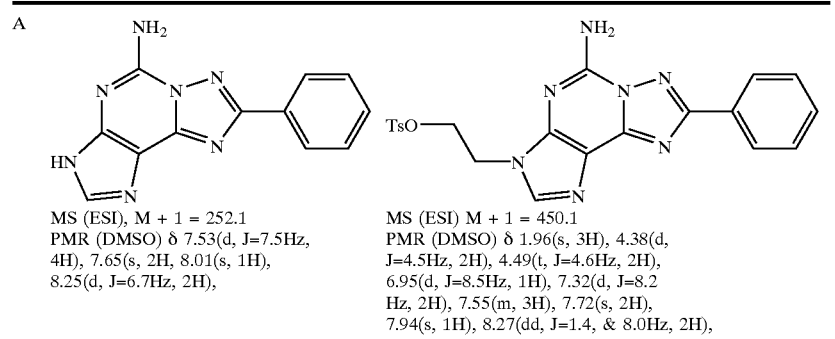

A

MS (ESI), M + 1 = 252.1
PMR (DMSO) δ 7.53(d, J=7.5Hz, 4H), 7.65(s, 2H, 8.01(s, 1H), 8.25(d, J=6.7Hz, 2H),

MS (ESI) M + 1 = 450.1
PMR (DMSO) δ 1.96(s, 3H), 4.38(d, J=4.5Hz, 2H), 4.49(t, J=4.6Hz, 2H), 6.95(d, J=8.5Hz, 1H), 7.32(d, J=8.2 Hz, 2H), 7.55(m, 3H), 7.72(s, 2H), 7.94(s, 1H), 8.27(dd, J=1.4, & 8.0Hz, 2H),

-continued

B 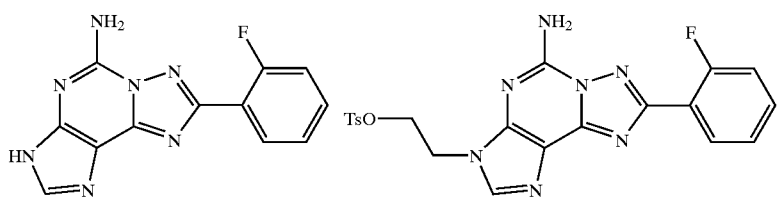

MS (ESI), M + 1 = 270
PMR (DMSO) δ 7.38(m, 3H), 7.57(m, 1H), 7.85(bs, 2H), 8.17 (dt, 1H), 8.50(s, 1H),

MS (ESI) M + 1 = 468.1
PMR (DMSO) δ 1.97(s, 3H), 4.39(t, 2H), 4.49(t, 2H), 6.94(d, 2H), 7.31(d, 2H), 7.41(m, 2H), 7.60(m, 1H), 7.70 (bs, 2H), 7.96(s, 1H), 8.21(dt, 2H),

C 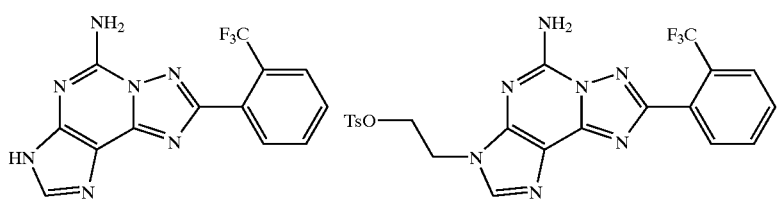

MS (ESI), M + 1 = 320.1
PMR (DMSO) δ 7.63(s, 2H), 7.80 (m, 3H), 7.92(m, 2H), 8.05(s, 1H)

MS (ESI) M + 1 = 518
PMR (DMSO) δ 2.06(s, 3H), 4.43(m, 4H), 6.97(d, J=7.0Hz, 2H), 7.33(d, J= 7Hz, 2H), 7.74–7.97(m, 7H),

D 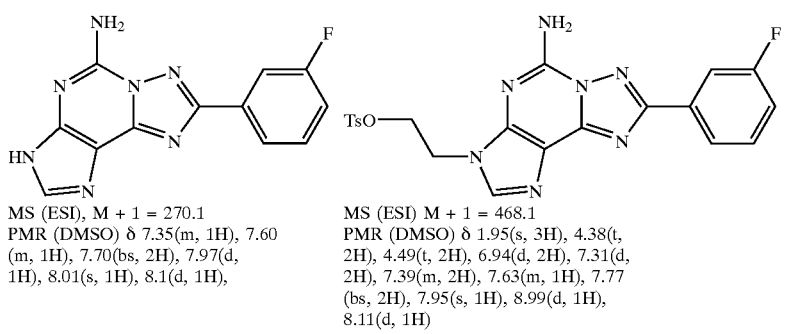

MS (ESI), M + 1 = 270.1
PMR (DMSO) δ 7.35(m, 1H), 7.60 (m, 1H), 7.70(bs, 2H), 7.97(d, 1H), 8.01(s, 1H), 8.1(d, 1H),

MS (ESI) M + 1 = 468.1
PMR (DMSO) δ 1.95(s, 3H), 4.38(t, 2H), 4.49(t, 2H), 6.94(d, 2H), 7.31(d, 2H), 7.39(m, 2H), 7.63(m, 1H), 7.77 (bs, 2H), 7.95(s, 1H), 8.99(d, 1H), 8.11(d, 1H)

E 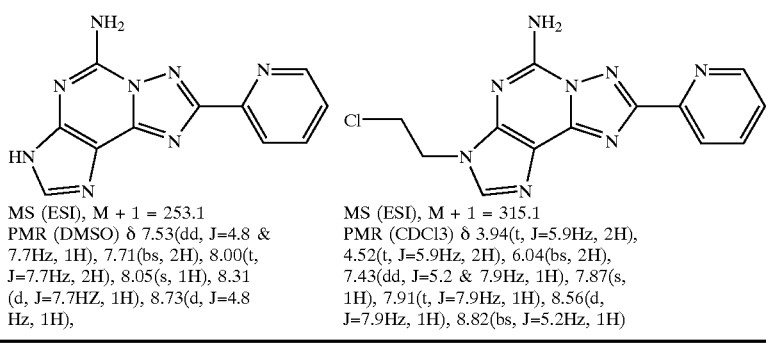

MS (ESI), M + 1 = 253.1
PMR (DMSO) δ 7.53(dd, J=4.8 & 7.7Hz, 1H), 7.71(bs, 2H), 8.00(t, J=7.7Hz, 2H), 8.05(s, 1H), 8.31 (d, J=7.7HZ, 1H), 8.73(d, J=4.8 Hz, 1H),

MS (ESI), M + 1 = 315.1
PMR (CDCl3) δ 3.94(t, J=5.9Hz, 2H), 4.52(t, J=5.9Hz, 2H), 6.04(bs, 2H), 7.43(dd, J=5.2 & 7.9Hz, 1H), 7.87(s, 1H), 7.91(t, J=7.9Hz, 1H), 8.56(d, J=7.9Hz, 1H), 8.82(bs, J=5.2Hz, 1H)

EXAMPLE 1

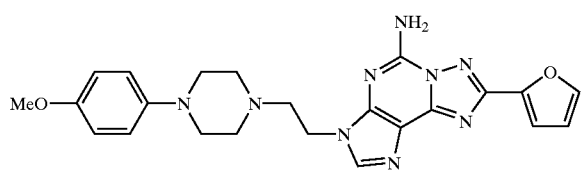

Combine the product of Preparation 1 (0.17 g, 0.39 mmol) and 1-(4 methoxy) phenyl piperazine (0.18 g, 0.77 mmol) in DMF and heat at 90° C. for 20 h. Concentrate and purify by flash column chromatography to obtain the title compound as a white solid, MS (ESI), M+1=430.1

In a similar fashion, using the appropriately substituted piperazine, the following compounds were prepared:

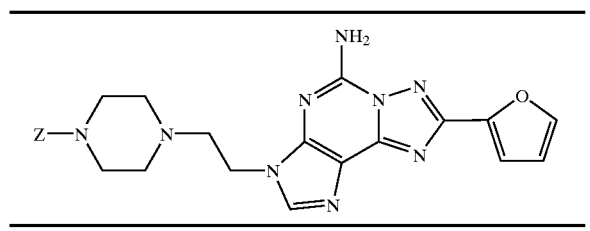

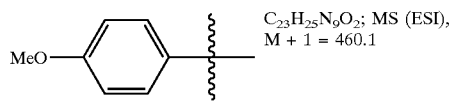
C₂₃H₂₅N₉O₂; MS (ESI), M + 1 = 460.1

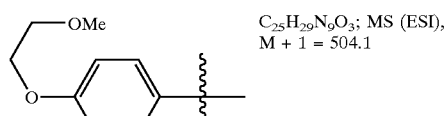
C₂₅H₂₉N₉O₃; MS (ESI), M + 1 = 504.1

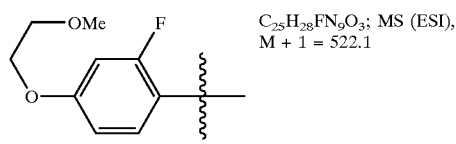
C₂₅H₂₈FN₉O₃; MS (ESI), M + 1 = 522.1

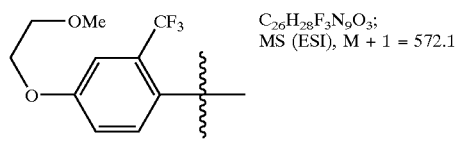
C₂₆H₂₈F₃N₉O₃; MS (ESI), M + 1 = 572.1

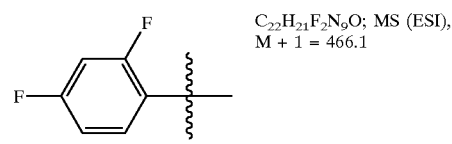
C₂₂H₂₁F₂N₉O; MS (ESI), M + 1 = 466.1

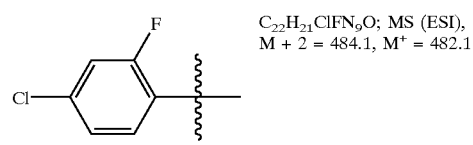
C₂₂H₂₁ClFN₉O; MS (ESI), M + 2 = 484.1, M⁺ = 482.1

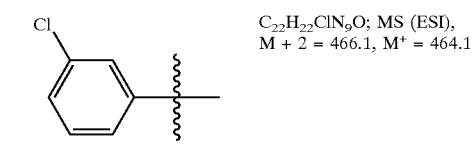
C₂₂H₂₂ClN₉O; MS (ESI), M + 2 = 466.1, M⁺ = 464.1

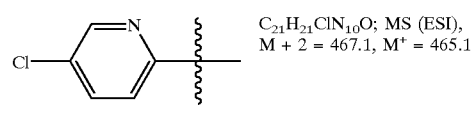
C₂₁H₂₁ClN₁₀O; MS (ESI), M + 2 = 467.1, M⁺ = 465.1

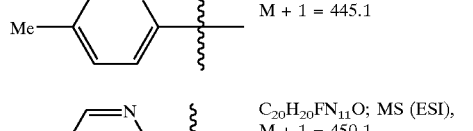
C₂₂H₂₄N₁₀O; MS (ESI), M + 1 = 445.1

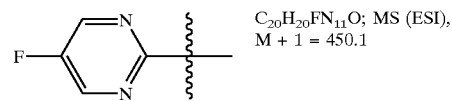
C₂₀H₂₀FN₁₁O; MS (ESI), M + 1 = 450.1

-continued

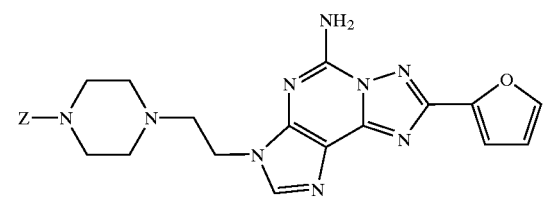

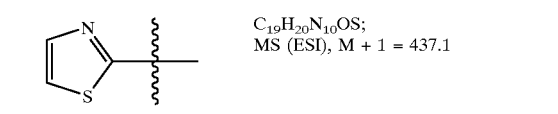
C₁₉H₂₀N₁₀OS; MS (ESI), M + 1 = 437.1

EXAMPLE 2

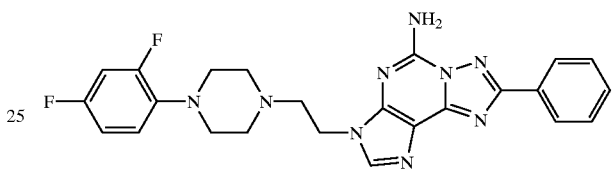

Combine the product of Preparation 1A and 1-(2,4-difluoro phenyl) piperazine in DMF and heat at 80° C. for 20 h. Concentrate and purify by flash column chromatography to obtain the title compound as a white solid, Mass spectrum (ESI), M+1=476.1.

In similar fashion, the following compounds were prepared:

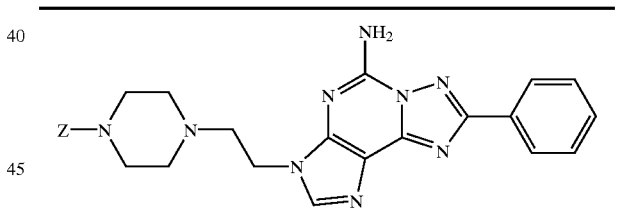

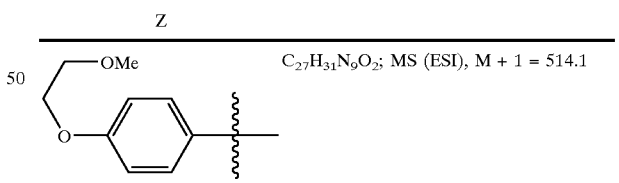
C₂₇H₃₁N₉O₂; MS (ESI), M + 1 = 514.1

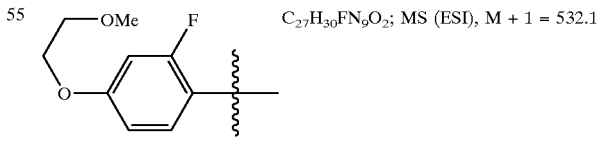
C₂₇H₃₀FN₉O₂; MS (ESI), M + 1 = 532.1

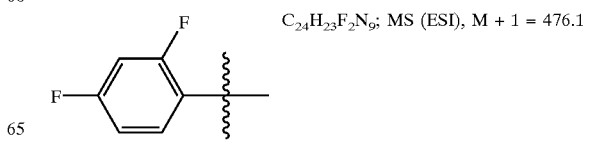
C₂₄H₂₃F₂N₉; MS (ESI), M + 1 = 476.1

-continued
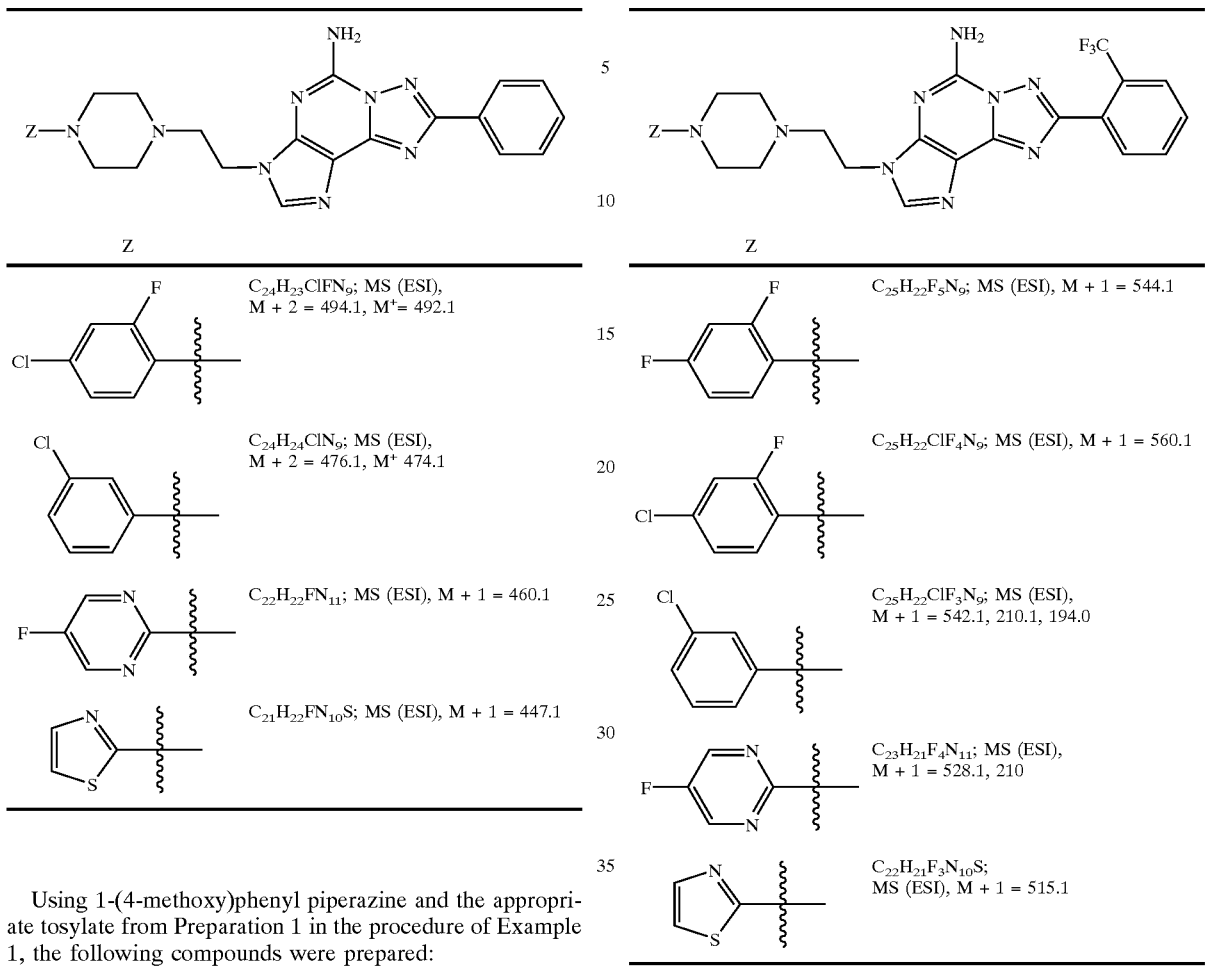
Using 1-(4-methoxy)phenyl piperazine and the appropriate tosylate from Preparation 1 in the procedure of Example 1, the following compounds were prepared:
EXAMPLE 3
EXAMPLE 4
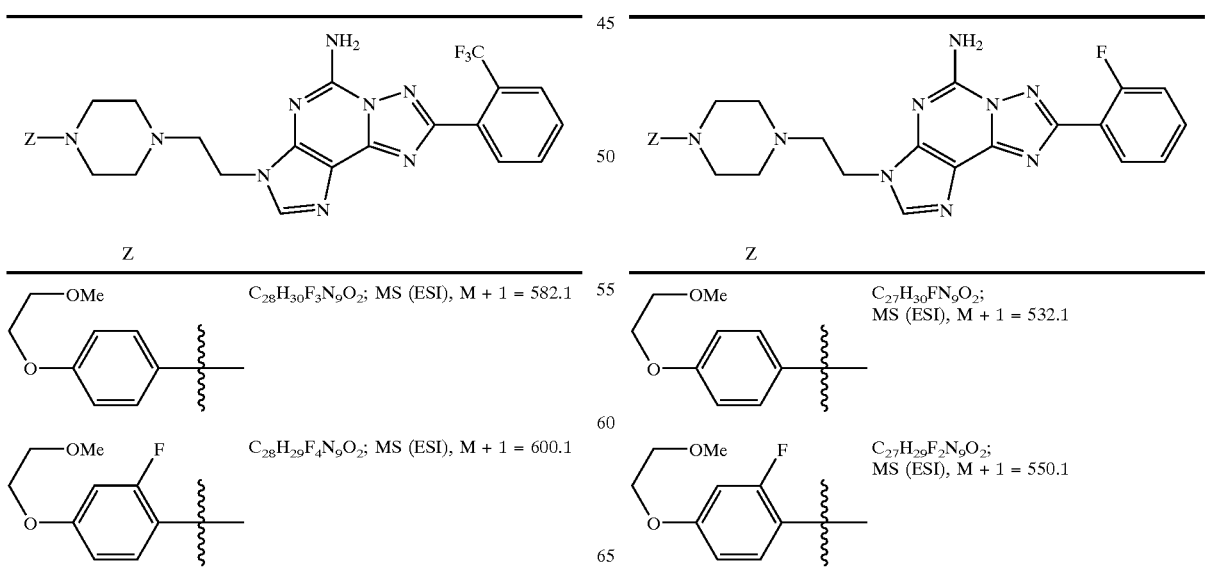

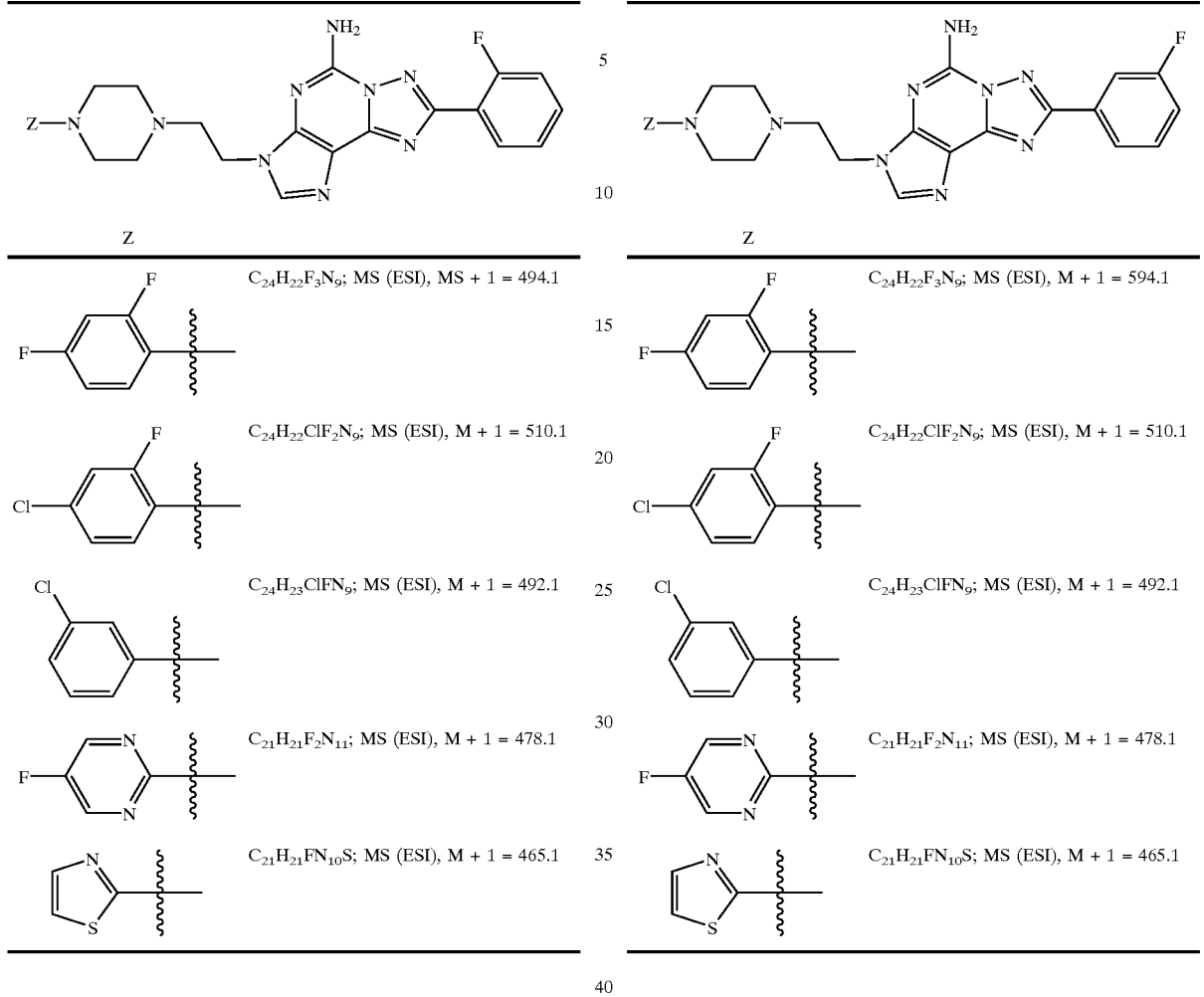
EXAMPLE 5
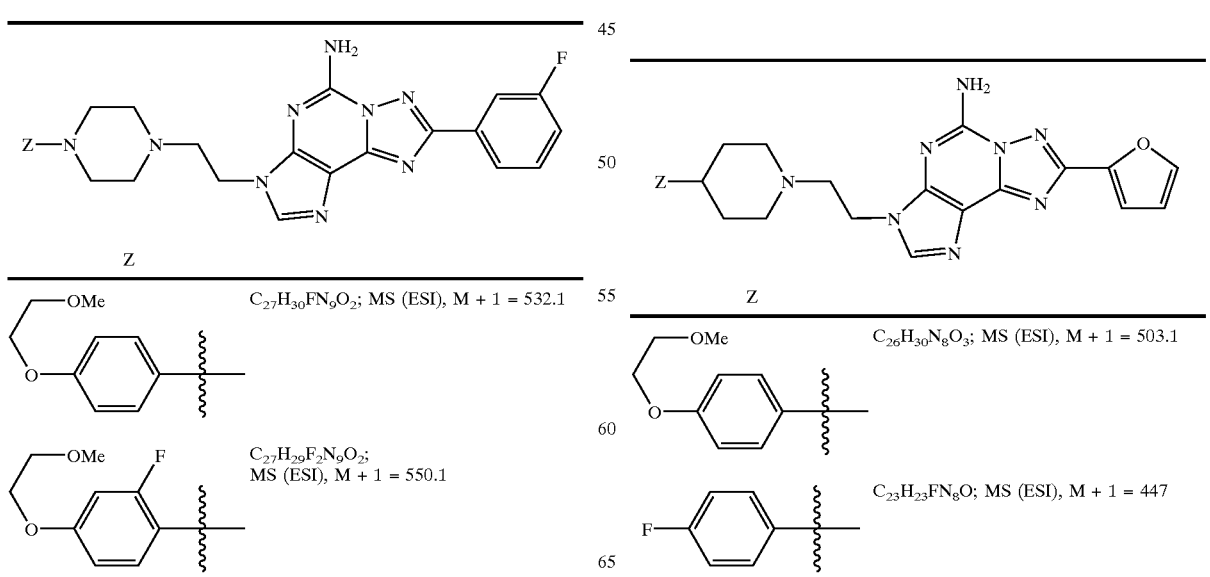
EXAMPLE 6

-continued

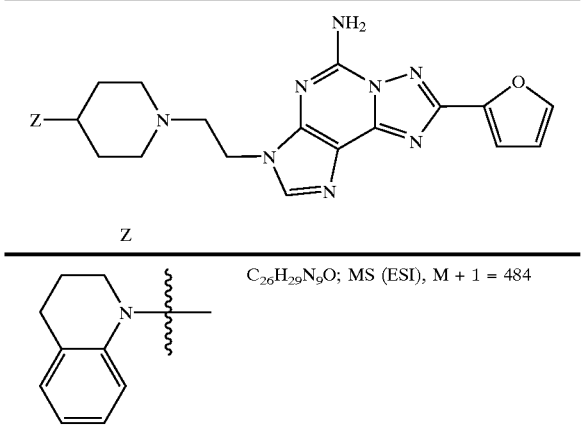

Z $C_{26}H_{29}N_9O$; MS (ESI), M + 1 = 484

EXAMPLE 7

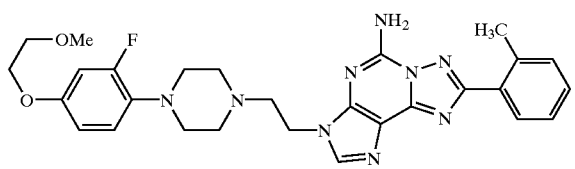

Using the appropriate piperazine and the appropriate tosylate made by a procedure analogous to Preparation 1 in the procedure of Example 1, the title compound was prepared. Mass spectrum (ESI) M+1=547.1 ($C_{28}H_{33}FN_9O_2$).

EXAMPLE 8

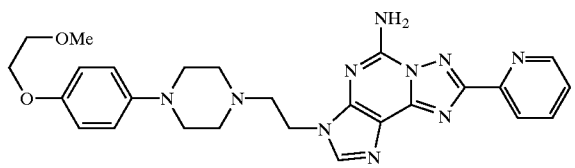

Using the appropriate piperazine and the chloride of Preparation 1 E in the procedure of Example 1, the title compound was prepared. Mass spectrum (ESI) M+1=528.1 ($C_{26}H_{30}N_{10}O_2$).

Because of their adenosine $A_{2a}$ receptor antagonist activity, compounds of the present invention are useful in the treatment of depression, cognitive function diseases and neurodegenerative diseases such as Parkinson's disease, senile dementia as in Alzheimer's disease, and psychoses of organic origin. In particular, the compounds of the present invention can improve motor-impairment due to neurodegenerative diseases such as Parkinson's disease.

The other agents known to be useful in the treatment of Parkinson's disease that can be administered in combination with the compounds of formula I include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; and COMT inhibitors such as tolcapone and entacapone. One to three other agents can be used in combination with the compounds of formula I, preferably one.

The pharmacological activity of the compounds of the invention was determined by the following in vitro and in vivo assays to measure $A_2$ receptor activity.

Human Adenosine $A_{2a}$ and $A_1$ Receptor Competition Binding Assay Protocol

Membrane sources:

$A_2a$: Human $A_{2a}$ Adenosine Receptor membranes, Catalog #RB-HA2a, Receptor Biology, Inc., Beltsville, Md. Dilute to 17 µg/100 µl in membrane dilution buffer (see below).

Assay Buffers:

Membrane dilution buffer: Dulbecco's Phosphate Buffered Saline (Gibco/BRL)+10 mM $MgCl_2$.

Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.

Ligands:

$A_{2a}$: [3H]—SCH 58261, custom synthesis, AmershamPharmacia Biotech, Piscataway, N.J. Stock is prepared at 1 nM in membrane dilution buffer. Final assay concentration is 0.5 nM.

$A_1$: [3H]-DPCPX, AmershamPharmacia Biotech, Piscataway, N.J. Stock is prepared at 2 nM in membrane dilution buffer. Final assay concentration is 1 nM.

Non-specific Binding:

$A_2$a: To determine non-specific binding, add 100 nM CGS 15923 (RBI, Natick, Mass.) Working stock is prepared at 400 nM in compound dilution buffer.

$A_1$: To determine non-specific binding, add 100 µM NECA (RBI, Natick, Mass.). Working stock is prepared at 400 µM in compound dilution buffer.

Compound Dilution:

Prepare 1 mM stock solutions of compounds in 100% DMSO. Dilute in compound dilution buffer. Test at 10 concentrations ranging from 3 µM to 30 µM. Prepare working solutions at 4× final concentration in compound dilution buffer.

Assay procedure:

Perform assays in deep well 96 well plates. Total assay volume is 200 µl. Add 50 µl compound dilution buffer (total ligand binding) or 50 µl CGS 15923 working solution ($A_{2a}$ non-specific binding) or 50 µl NECA working solution (Al non-specific binding) or 50 µl of drug working solution. Add 50 µl ligand stock ([3H]—SCH 58261 for $A_{2a}$, [3H]-DPCPX for $A_1$). Add 100 µl of diluted membranes containing the appropriate receptor. Mix. Incubate at room temperature for 90 minutes. Harvest using a Brandel cell harvester onto Packard GF/B filter plates. Add 45 µl Microscint 20 (Packard), and count using the Packard TopCount Microscintillation Counter. Determine $IC_{50}$ values by fitting the displacement curves using an iterative curve fitting program (Excel). Determine Ki values using the Cheng-Prusoff equation.

Haloperidol-induced Catalepsy in the Rat

Male Sprague-Dawley rats (Charles River, Calco, Italy) weighing 175–200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglass cage placed at an angle of about 70 degrees with the bench table. The rat is placed on the grid with all four legs abducted and extended ("frog posture"). The use of such an unnatural posture is essential for the specificity of this test for catalepsy. The time span from placement of the paws until the first complete removal of one paw (decent latency) is measured maximally for 120 sec.

The selective $A_{2A}$ adenosine antagonists under evaluation are administered orally at doses ranging between 0.3 and 3 mg/kg, 1 and 4 h before scoring the animals.

In separate experiments, the anticataleptic effects of the reference compound, L-DOPA (25, 50 and 100 mg/kg, ip), were determined.

6-OHDA Lesion of the Middle Forebrain Bundle in Rats

Adult male Sprague-Dowley rats (Charles River, Calco, Como, Italy), weighing 275–300 g, are used in all experiments. The rats are housed in groups of 4 per cage, with free access to food and water, under controlled temperature and 12 hour light/dark cycle. The day before the surgery the rats are fasted over night with water ad libitum.

Unilateral 6-hydroxydopamine (6-OHDA) lesion of the middle forebrain bundle is performed according to the method described in Ungerstedt et al, *Brian Research*, 24 (1970), p. 485–493, and Ungerstedt, *Eur. J. Pharmacol.*, 5 (1968), p. 107–110, with minor changes. Briefly, the animals are anaesthetized with chloral hydrate (400 mg/kg, ip) and treated with desipramine (10 mpk, ip) 30 min prior to 6-OHDA injection in order to block the uptake of the toxin by the noradrenergic terminals. Then, the animals are placed in a stereotaxic frame. The skin over the skull is reflected and the stereotaxic coordinates (−2.2 posterior from bregma (AP), +1.5 lateral from bregma (ML), 7.8 ventral from dura (DV) are taken, according to the atlas of Pellegrino et al (Pellegrino L. J., Pellegrino A. S. and Cushman A. J., *A Stereotaxic Atlas of the Rat Brain*, 1979, New York: Plenum Press). A burr hole is then placed in the skull over the lesion site and a needle, attached to a Hamilton syringe, is lowered into the left MFB. Then 8 $\mu$g 6-OHDA-HCl is dissolved in 4 $\mu$l of saline with 0.05% ascorbic acid as antioxidant, and infused at the constant flow rate of 1 $\mu$l/1 min using an infusion pump. The needle is withdrawn after additional 5 min and the surgical wound is closed and the animals left to recover for 2 weeks.

Two weeks after the lesion the rats are administered with L-DOPA (50 mg/kg, ip) plus Benserazide (25 mg/kg, ip) and selected on the basis of the number of full contralateral turns quantified in the 2 h testing period by automated rotameters (priming test). Any rat not showing at least 200 complete turns/2 h is not included in the study.

Selected rats receive the test drug 3 days after the priming test (maximal dopamine receptor supersensitivity). The new $A_{2A}$ receptor antagonists are administered orally at dose levels ranging between 0.1 and 3 mg/kg at different time points (i.e., 1, 6, 12 h) before the injection of a subthreshold dose of L-DOPA (4 mpk, ip) plus benserazide (4 mpk, ip) and the evaluation of turning behavior.

Using the above test procedures, the following results were obtained for preferred and/or representative compounds of the invention.

Results of the binding assay on compounds of the invention showed $A_{2a}$ Ki vaules of 0.3 to 1000 nM, with preferred compounds showing Ki values between 0.3 and 50 nM.

Selectivity is determined by dividing Ki for A1 receptor by Ki for A2a receptor. Preferred compounds of the invention have a selectivity ranging from about 100 to about 2000.

Preferred compounds showed about a 50–75% decrease in descent latency when tested orally at 1–3 mg/kg for anticataleptic activity in rats.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen for compounds of formula I is oral administration of from 10 mg to 2000 mg/day preferably 10 to 1000 mg/day, in two to four divided doses to provide relief from central nervous system diseases such as Parkinson's disease. The compounds are non-toxic when administered within this dosage range.

The doses and dosage regimen of the dopaminergic agents will be determined by the attending clinician in view of the approved doses and dosage regimen in the package insert, taking into consideration the age, sex and condition of the patient and the severity of the disease. It is expected that when the combination of a compound of formula I and a dopaminergic agent is administered, lower doses of the components will be effective compared to the doses of the components administered as monotherapy.

The following are examples of pharmaceutical dosage forms which contain a compound of the invention. Those skilled in the art will recognize that dosage forms can be modified to contain both a compound of formula I and a dopaminergic agent. The scope of the invention in its pharmaceutical composition aspect is not to be limited by the examples provided.

Pharmaceutical Dosage Form Examples

EXAMPLE A-Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| Total | | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B-Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| Total | | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound represented by the structural formula

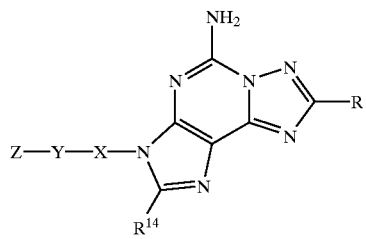

or a pharmaceutically acceptable salt thereof, wherein

R is $R^1$-heteroaryl, $R^{10}$-phenyl, $C_4$–$C_6$ cycloalkenyl, —C(=$CH_2$)$CH_3$, —C≡C—$CH_3$, —C≡C—$CH_2$—$OR^2$, —CH=C($CH_3$)$_2$,

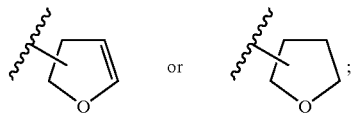

X is $C_1$–$C_6$ alkylene, —C(O)$CH_2$— or —C(O)N($R^2$)$CH_2$—;

Y is —N($R^2$)$CH_2CH_2$N($R^3$)—, —O$CH_2CH_2$N($R^2$)—, —O—, —S—, —$CH_2$S—, —($CH_2$)$_{2-3}$—N($R^2$)—, $R^5$-divalent heteroaryl,

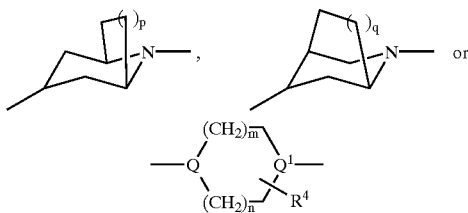

and

Z is $R^5$-phenyl, $R^5$-phenyl($C_1$–$C_6$)alkyl, $R^5$-heteroaryl, $R^5$-bicyclic heteroaryl, $R^5$-benzofused heteroaryl, diphenylmethyl or $R^6$–C(O)—;

or when Y is

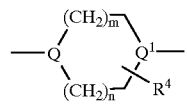

Z is also $R^6$—$SO_2$—, $R^7$—N(R)—C(O)—, $R^7$—N($R^8$)—C(S)— or $R^6$OC(O)—;

or when Q is

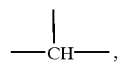

Z is also phenylamino or pyridylamino;

or Z and Y together are

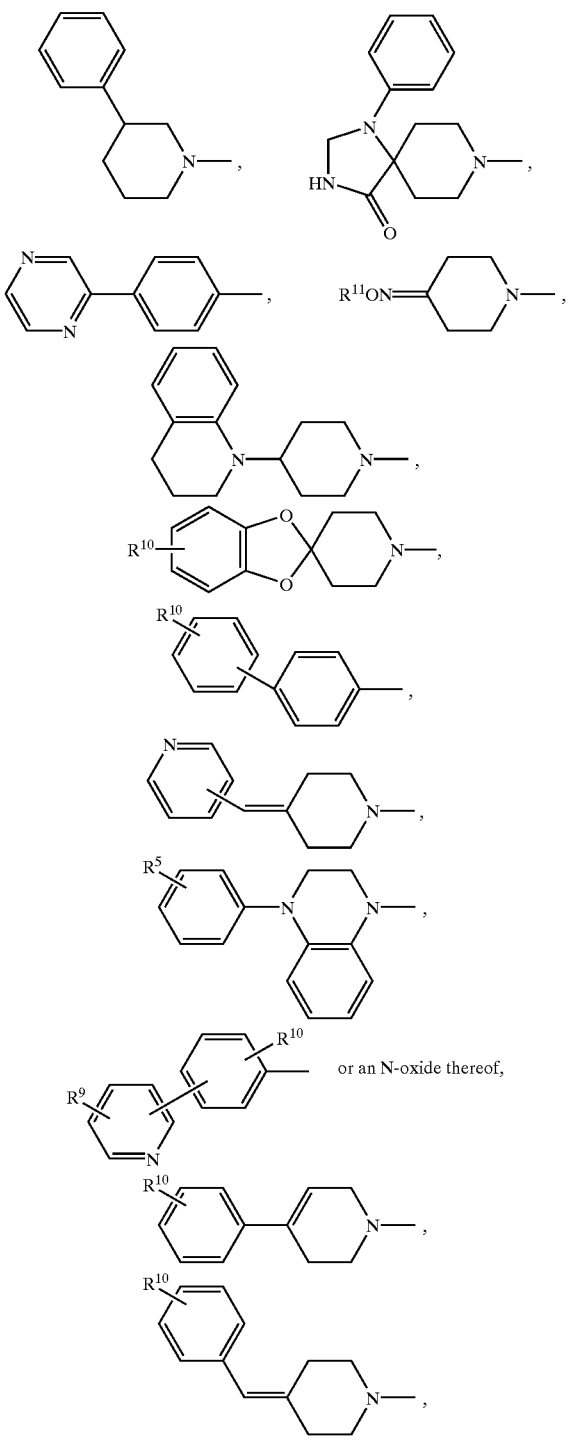

or an N-oxide thereof, or Y and Z together form a piperidinyl or pyrrolidinyl ring fused to a monocyclic or bicyclic aryl or a monocyclic or bicyclic heteroaryl ring wherein X is attached to the N atom of the piperidinyl or pyrrolidinyl ring;

$R_1$ is 1 to 3 substituents independently selected from hydrogen, $C_1$–$C_6$-alkyl, —$CF_3$, halogen, —$NO_2$, —$NR^{12}R^{13}$, $C_1$–$C_6$ alkoxy, $C_1$–$C_6$ alkylthio, $C_1$–$C_6$ alkylsulfinyl, $C_1$–$C_6$ alkylsulfonyl, —$COOR^7$ or —$C(O)NR^2R^3$;

$R^2$ and $R^3$ are independently selected from the group consisting of hydrogen and $C_1$–$C_6$ alkyl;

m and n are independently 2–3;

p and q are independently 0–2;

Q and $Q^1$ are independently selected from the group consisting of

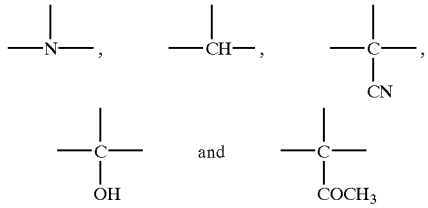

provided that at least one of Q and $Q^1$ is

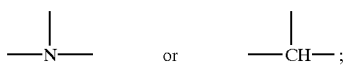

$R^4$ is 1–2 substituents independently selected from the group consisting of hydrogen, $C_1$–$C_6$alkyl, $R^1$-aryl and $R^1$-heteroaryl, or two $R^4$ substituents on the same carbon can form =O;

$R^5$ is 1 to 5 substituents independently selected from the group consisting of hydrogen, halogen, $C_1$–$C_6$ alkyl, hydroxy, $C_1$–$C_6$ alkoxy, —CN, di-(($C_1$–$C_6$)alkyl) amino, —$CF_3$, —$OCF_3$, acetyl, —$NO_2$, hydroxy ($C_1$–$C_6$)alkoxy, ($C_1$–$C_6$)-alkoxy($C_1$–$C_6$)alkoxy, di-(($C_1$–$C_6$)-alkoxy)($C_1$–$C_6$)alkoxy, ($C_1$–$C_6$)-alkoxy ($C_1$–$C_6$)alkoxy-($C_1$–$C_6$)-alkoxy, carboxy($C_1$–$C_6$)-alkoxy, ($C_1$–$C_6$)-alkoxycarbonyl($C_1$–$C_6$)alkoxy, ($C_3$–$C_6$)cycloalkyl($C_1$–$C_6$)alkoxy, di-(($C_1$–$C_6$)alkyl) amino($C_1$–$C_6$)alkoxy, morpholinyl, ($C_1$–$C_6$)alkyl-$SO_2$—, ($C_1$–$C_6$)alkyl-$SO_2$-($C_1$–$C_6$)alkoxy, tetrahydropyranyloxy, ($C_1$–$C_6$)alkylcarbonyl($C_1$–$C_6$)-alkoxy, ($C_1$–$C_6$)-alkoxycarbonyl, ($C_1$–$C_6$) alkylcarbonyloxy($C_1$–$C_6$)-alkoxy, —$SO_2NH_2$, phenoxy,

$(R^2O)_2$-P(O)—$CH_2$—O— and $(R^2O)_2$—P(O)—; or adjacent $R^5$ substituents together are —O—$CH_2$—O—, —O—$CH_2CH_2$—O—, —O—$CF_2$—O— or —O—$CF_2CF_2$—O— and form a ring with the carbon atoms to which they are attached;

$R^6$ is ($C_1$–$C_6$)alkyl, $R^5$-phenyl, $R^5$-phenyl($C_1$–$C_6$)alkyl, thienyl, pyridyl, ($C_3$–$C_6$)-cycloalkyl, ($C_1$–$C_6$)alkyl-OC (O)—NH—($C_1$–$C_6$)alkyl—, di-(($C_1$–$C_6$)alkyl )aminomethyl, or

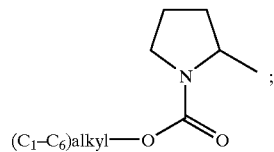

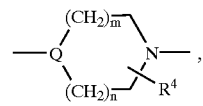

Q is

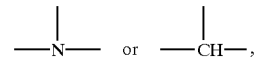

R[7] is (C₁–C₆)alkyl, R[5]-phenyl or R[5]-phenyl(C₁–C₆)alkyl;

R[8] is hydrogen or C₁–C₆ alkyl; or R[7] and R[8] together are —(CH₂)$_p$—A—(CH₂)$_q$, wherein p and q are independently 2 or 3 and A is a bond, —CH₂—, —S— or —O—, and form a ring with the nitrogen to which they are attached;

R[9] is 1–2 substituents independently selected from the group consisting of hydrogen, C₁–C₆ alkyl, hydroxy, C₁–C₆ alkoxy, halogen, —CF₃ and (C₁–C₆)alkoxy-(C₁–C₆)alkyl;

R[10] is 1 to 5 substituents independently selected from the group consisting of hydrogen, halogen, C₁–C₆ alkyl, hydroxy, C₁–C₆ alkoxy, —CN, —NH₂, C₁–C₆alkylamino, di-((C₁–C₆)alkyl)amino, —CF₃, —OCF₃, —S(O)$_{0-2}$(C₁–C₆)alkyl and —CH₂—SO₂-phenyl;

R[11] is H, C₁–C₆ alkyl, phenyl, benzyl, C₂–C₆ alkenyl, C₁–C₆ alkoxy(C₁–C₆)alkyl, di-((C₁–C₆)alkyl)amino (C₁–C₆)alkyl, pyrrolidinyl(C₁–C₆)alkyl or piperidino (C₁–C₆)alkyl;

R[12] is H or C₁–C₆ alkyl;

R[13] is H, (C₁–C₆)alkyl—C(O)— or (C₁–C₆)alkyl—SO₂—;

R[14] is H, halogen, C₁–C₆ alkyl, hydroxy(C₁–C₆)alkyl, C₁–C₆ alkoxy(C₁–C₆)alkyl, thio(C₁–C₆)alkyl, (C₁–C₆)alkylthio(C₁–C₆)alkyl or NR²R³—(C₁–C₆)alkyl; and R[15] is H, halogen, C₁–C₆ alkyl or C₁–C₆ alkoxy.

2. A compound of claim 1 wherein R is R[1]-furanyl.

3. A compound of claim 1 wherein X is C₂–C₆ alkylene.

4. A compound of claim 1 wherein Y is

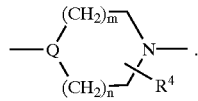

5. A compound of claim 4 wherein Q is

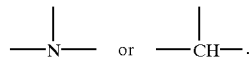

6. A compound of claim 5 wherein m and n are each 2, and R[4] is H.

7. A compound of claim 1 wherein Z is R[5]-phenyl or R[5]-heteroaryl.

8. A compound of claim 7 wherein R[5] is H, halogen, C₁–C₆ alkyl, C₁–C₆ alkoxy, hydroxy(C₁–C₆)alkoxy or (C₁–C₆)alkoxy(C₁–C₆)alkoxy.

9. A compound of claim 1 wherein R is R[1]-furanyl, X is C₂–C₆ alkylene, Y is m and n are each 2, R[4] is H, Z is R[5]-phenyl or R[5]-heteroaryl, and R[5] is H, halogen, C₁–C₆ alkyl, C₁–C₆ alkoxy, hydroxy(C₁–C₆)alkoxy or (C₁–C₆)-alkoxy(C₁–C₆)alkoxy.

10. A compound of claim 1 selected from the group consisting of

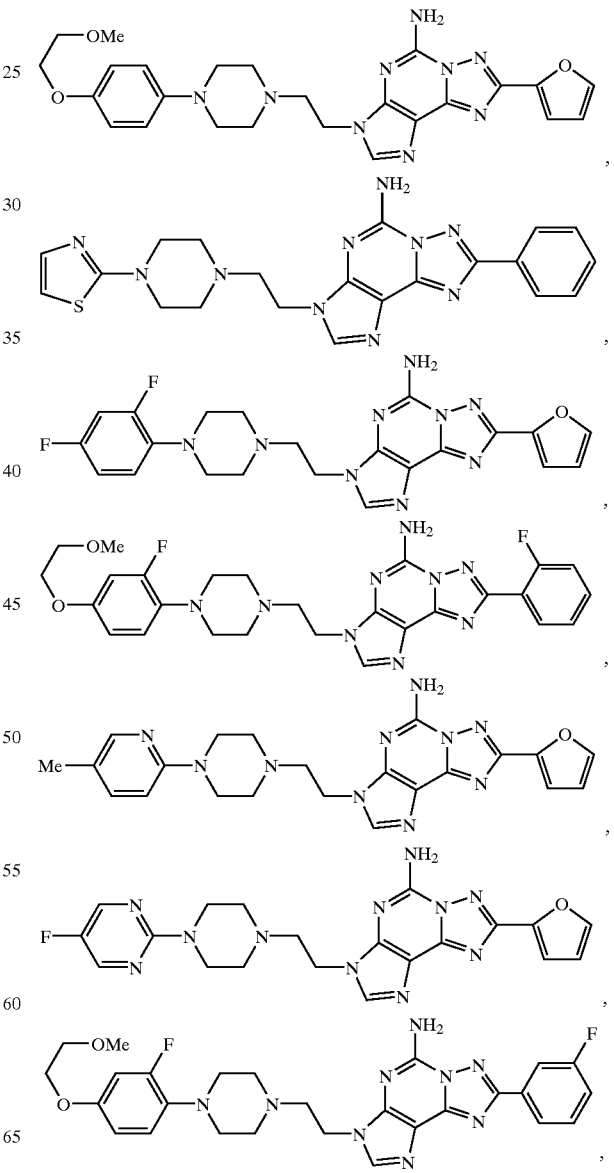

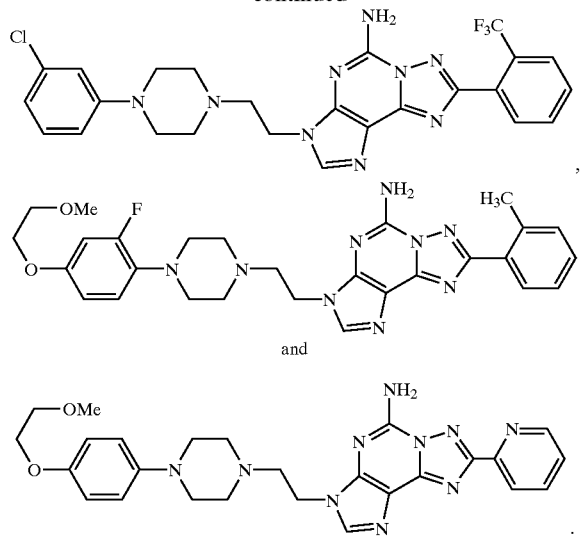

11. A pharmaceutical composition comprising a therapeutically effective amount of a compound of claim 1 in a pharmaceutically acceptable carrier.

12. A method of treating stroke, depression, Parkinson's disease, senile dementia or psychoses of organic origin comprising administering an effective amount of a compound of claim 1 to a mammal in need of such treatment.

13. A pharmaceutical composition comprising a therapeutically effective amount of a combination of a compound of claim 1 and 1 to 3 other agents useful in treating Parkinson's disease in a pharmaceutically acceptable carrier.

14. A method of treating Parkinson's disease comprising administering to a mammal in need of such treatment an effective amount of a combination of a compound of claim 1 and 1 to 3 other agents useful in treating Parkinson's disease.

15. The method of claim 14 wherein the other agents are selected from the group consisting of L-DOPA, dopaminergic agonists, MAO-B inhibitors, DOPA decarboxylase inhibitors and COMT inhibitors.

* * * * *